United States Patent [19]

Bathelt et al.

[11] 4,147,743

[45] Apr. 3, 1979

[54] AMPHOLYTIC, FLUORINE-CONTAINING ESTERS OF PHOSPHOROUS ACID

[75] Inventors: Heinrich Bathelt, Altötting; Siegfried Billenstein, Burgkirchen, Alz; Erich Schuierer, Burghausen, Salzach, all of Fed. Rep. of Germany

[73] Assignee: Hoechst Aktiengesellschaft, Frankfurt am Main, Fed. Rep. of Germany

[21] Appl. No.: 859,051

[22] Filed: Dec. 9, 1977

[30] Foreign Application Priority Data

Dec. 13, 1976 [DE] Fed. Rep. of Germany ....... 2656424

[51] Int. Cl.$^2$ .......................... C07F 9/141; C11D 9/36
[52] U.S. Cl. ................................... 260/924; 252/89R; 252/89 DC
[58] Field of Search ......................... 260/924

[56] References Cited

U.S. PATENT DOCUMENTS

| 3,856,893 | 12/1974 | Diery et al. | 260/924 OR |
| 3,888,978 | 6/1975 | Duwel et al. | 260/924 X |
| 3,928,509 | 12/1975 | Diery et al. | 260/924 X |

*Primary Examiner*—Anton H. Sutto
*Attorney, Agent, or Firm*—Connolly and Hutz

[57] ABSTRACT

Compounds of the formula

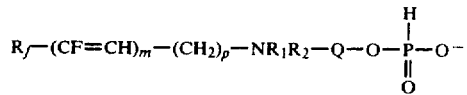

wherein $R_f$ is a perfluoroalkyl group of 3 to 16 carbon atoms, $R_1$ and $R_2$ is hydrogen, lower alkyl of 1 to 4 carbon atoms, cyclohexyl, 2-hydroxyalkyl, or $R_f-(CF=CH)_m-(CH_2)_p-$, Q is $-(CH_2)_x-$, $-CH_2-CHR-$, or $-CH_2-CRR'-CH_2-$ (R is lower alkyl or phenyl, R' is lower alkyl, phenyl or hydrogen), x is an integer of 2 or 3, m is an integer of 0 or 1 and p is an integer of 1 to 4, are prepared by reacting florinated amines of the formula

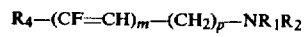

with cyclic phosphites of the formula

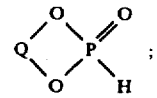

these compounds are useful for lowering the surface tension in aqueous solutions and as wetting agents in dry-cleaning processes for textiles.

1 Claim, No Drawings

AMPHOLYTIC, FLUORINE-CONTAINING ESTERS OF PHOSPHOROUS ACID

The invention relates to ampholytic, fluorine-containing esters of phosphorous acid of the general formula

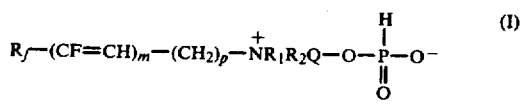

in which $R_f$ represents a perfluoroalkyl radical having 3 to 16 C atoms, $R_1$ and $R_2$ which can be identical or different represent hydrogen atoms, short-chain alkyl radicals having 1 to 4 C atoms, cyclohexyl radicals, 2-hydroxyalkyl radicals or the radical $R_f-(CF=CH)_m-(CH_2)_p$ and Q represents alkylene radicals $-(CH_2)_x-$ with $x = 2$ or 3 and alkylene radicals $-CH_2CHR-$ or $-CH_2CRR'-CH_2-$ with R and R' being a short-chain alkyl radical or a phenyl radical, it also being possible for R' to be H, and in which, furthermore, m is 0 or 1 and p is an integer from 1 to 4.

In the general formula indicated above, $R_f$ preferably represents a perfluoroalkyl radical having 5 to 12 C atoms, and straight-chain perfluoroalkyl radicals are particularly preferred. $R_1$ and $R_2$ which can be identical or different are preferably straight-chain alkyl radicals having 1 to 4, in particular 1 to 2, C atoms, and also the 2-hydroxyethyl radical, one of the two radicals $R_1$ to $R_2$ being especially a 2-hydroxyethyl radical. $R_1$ or $R_2$ can also preferably denote a radical of the formula $R_f(CF=CH)_m-(CH_2)_p$, and p here preferably is an integer from 1 to 3 and m can be 1 or preferably 0. For Q, in addition to radicals of the structure $-(CH_2)_x-$ with $x = 2$ or 3, those of the structure $-CH_2CHR-$ and $-CH_2CRR'-CH_2-$ are preferred in which R and R' are an alkyl radical having 1 to 2 C atoms and, in particular, are a methyl radical. Preferably, R' can also be a phenyl radical. The index p preferably assumes integral values from 1 to 3.

The invention also relates to a process for the manufacture of ampholytic, fluorine-containing esters of phosphorous acid of the abovementioned general formula I, in which $R_f$, $R_1$, $R_2$, Q, m and p have the abovementioned meaning (also with respect to the preferred limits), in which process amines of the general formula

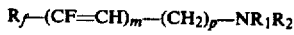

in which $R_f$, $R_1$, $R_2$, m and p have the abovementioned meaning, are reacted with cyclic phosphites of the general formula

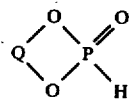

in which Q has the abovementioned meaning, at temperatures between $+20°$ C. and $+140°$ C., in bulk or in the presence of polar solvents. In particular, this process according to the invention is carried out with amines of the abovementioned formula and cyclic phosphites of the abovementioned formula, in which $R_f$, $R_1$, $R_2$, Q, m and p have the preferred meaning mentioned.

The said reaction is advantageously carried out at a temperature between $+20°$ and $+140°$ C., preferably between $+60°$ and $+140°$ C. It is appropriate here to initially introduce the fluorine-containing amine, warmed to the reaction temperature, and slowly to add the cyclic phosphorous acid ester, used as the alkylating agent, until the amounts are in an equimolar ratio. It is also advisable to blanket the reaction mixture with an inert gas, such as, for example, nitrogen. The reaction is preferably carried out under normal pressure, but it is also possible to operate under reduced pressure or, especially in the presence of solvents, under a slightly elevated pressure. In principle, the reaction does not require a solvent. However, for easier handling of the starting materials and end products, which are very viscous at room temperature, it is advantageous to add polar solvents which appropriately are capable of dissolving both the starting materials and the end products. Polar solvents, such as methanol, ethanol, isopropanol, methylene chloride, chloroform as well as glycol and dimethyl glycol are particularly suitable. At the reaction temperatures of $+60°$ to $+120°$ C., which are generally used, the reaction has ended after about 2 to 4 hours. To increase the conversion and the reaction rate, it has proved to be particularly advantageous to add a relatively small amount of water, preferably 1 to 10 mole %, to the reaction process.

The fluorinated amines employed as the starting compounds can be manufactured, for example, in accordance with U.S. Pat. No. 3,535,381, U.S. Pat. No. 3,257,407, DT-OS No. 2,141,542 or DT-OS No. 1,768,939. For the further reaction with the cyclic esters of phosphorous acid, it is also possible successfully to employ mixtures of saturated and unsaturated fluorinated amines of the abovementioned formula, that is to say those amines in which m is 0 or 1. The cyclic esters of phosphorous acid, used as the further reaction component, are readily accessible from the corresponding 1,2- or 1,3-glycols and phosphorus trichloride by methods which are generally known (compare Houben-Weyl, Methoden der organischen Chemie, [Methods of Organic Chemistry], 4th edition, volume 12; 2, page 25 to 26). They can also be obtained directly by transesterification of dialkyl phosphites with the corresponding glycols (ibid. page 35 to 36).

The resulting yields of ampholytic, fluorine-containing esters of phosphorous acid according to the invention, of the formula I, are virtually quantitative and most of these compounds are excellently soluble in water. The solvent which may have been added can be separated off by distillation, if necessary under reduced pressure. In many cases, however, this is unnecessary since the compounds according to the invention are employed in the dissolved form, if necessary with the addition of water.

The examples which follow illustrate the manufacture of the compounds according to the invention:

EXAMPLE 1

399.2 g = 1.0 mole of $C_5F_{11}CF=CH-CH_2-N(C_2H_5)_2$, 500 ml of isopropanol and 5 ml of water are initially introduced into a glass flask which is equipped with a stirrer, reflux condenser, dropping funnel and thermometer, the mixture is heated up to the boiling point of isopropanol and 150.1 g (= 1.0 mole) of a cyclic phosphite of the formula

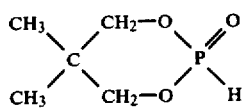

are then added in the course of 20 minutes. The reaction mixture is then boiled under reflux for a further 4 hours. After the reaction has ended, the isopropanol is distilled off and even small residual amounts of the solvent are removed by applying a water pump vacuum. This gives a light brown oil which is highly viscous at room temperature and which is soluble in water giving a clear solution.

Yield: 545.6 g = 99.3% of theory.

The nuclear magnetic resonance spectra of the substance showed the following signals:

$^1$H nuclear magnetic resonance spectrum (measured here and in the further examples using a 60 MHz instrument from Messrs. Japan Electron Optics Co. Ltd. at 25° C., with tetramethylsilane as an internal standard; the signals are indicated in ppm in accordance with the δ scale) in d$_4$-methanol:

| | | |
|---|---|---|
| 12.05 }  \P/H, 1.56 } /\\O | | doublet with a coupling constant of ~629 Hz |
| 5.7 to 6.8: | —CF=CH— | triplettized doublet |
| 3.6 to 4.1: | =CH—CH$_2$—N$^+$< | multiplet |
| 3.7 to 4.1: | HO$_2$P—OCH$_2$— | multiplet |
| 2.8 to 3.3: | —N$^+$(CH$_2$CH$_3$)$_2$ / \\CH$_2$— | superimposing multiplets |
| 1.1 to 1.4: | >N$^+$(CH$_2$CH$_3$)$_2$ | triplet |
| 0.9: | >C(CH$_3$)$_2$ | singlet |

$^{19}$F nuclear magnetic resonance spectrum (measured here and in the further examples using a 56 MHz spectrometer from Messrs. Japan Electron Optics Lab. Co. Ltd. at 25° C. with trifluoroacetic acid as an external standard, data in ppm), in CHCl$_3$:

| | |
|---|---|
| 2.6: | —CF$_3$ |
| 43.8 to 45.0: | =CF-13 CF$_2$—(CF$_2$)$_3$— |
| 47.5: | CF$_3$—CF$_2$— |
| 39.0: | =CF—CF$_2$— |

EXAMPLE 2

5 g of water and 237.0 g of a mixture of fluorine-containing amines of the formula

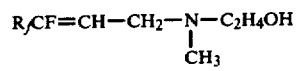

and of the following composition R$_f$ = C$_5$F$_{11}$ = 41.8% by weight, C$_7$F$_{15}$ = 34.4% by weight, C$_9$F$_{19}$ = 17.7% by weight and C$_{11}$F$_{23}$ = 6.1% by weight are initially introduced into a glass flask which is equipped with a stirrer, reflux condenser, dropping funnel and thermometer, the mixture is heated to about 80° C. and blanketed with nitrogen and 75.06 g of

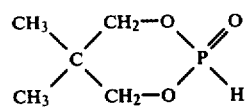

are then added in the course of half an hour.

The reaction mixture which initially consists of two phases is then heated up to 120° C., whilst stirring well, and kept at this temperature for 2 hours. After cooling, this gives 314 g of a brown, clear, highly viscous oil, which is very readily soluble in water without a residue (yield: 99.8% of theory). The nuclear magnetic resonance spectra of the substance shows the following signals:

$^1$H spectrum in d$_4$-methanol

| | | |
|---|---|---|
| 12.35 } \P/H, 1.45 } /\\O | | Doublet with a coupling constant of ~ 654 Hz |
| 7.6 to 7.9: | —CH$_2$OH | broad singlet |
| 5.7 to 6.7: | —CF=CH— | triplettized doublet |
| 3.7 to 4.4: | =CH—CH$_2$—N$^{\pm}$< | and HO$_2$P—OCH$_2$—multiplets |
| 2.8 to 3.4: | >N$^{\pm}$(CH$_2$—)(CH$_2$—) | and —CH$_2$OH multiplets |
| 2.8: | >N$^{\pm}$—CH$_3$ | singlet |
| 0.9: | >C(CH$_3$)$_2$ | singlet |

$^{19}$F spectrum in CHCl$_3$

| | |
|---|---|
| 30: | —CF$_3$ |
| 39.0: | —CH=CF—CF$_2$— |
| 43.4 to 44.2 | —(CF$_2$)$_n$— |
| 45.0: | —CF$_2$—CF=CH— |
| 48.0: | CF$_3$—CF$_2$= |

The following further compounds of the general formula I were prepared in accordance with the methods described in Example 1 and 2 (with and without solvent).

| Substance No. | Starting Formula | materials | Solvent | Reaction temperature Reaction time | Yield |
|---|---|---|---|---|---|
| 3 | $C_7F_{15}CF=CHCH_2-\overset{+}{\underset{C_2H_5}{\overset{C_2H_5}{N}}}-CH_2-\underset{CH_3}{\overset{CH_3}{C}}-CH_2O-\overset{O}{\underset{H}{P}}-O^-$ | $C_7F_{15}CF=CHCH_2-N\underset{C_2H_5}{\overset{C_2H_5}{\diagup}}$ $\underset{CH_3}{\overset{CH_3}{C}}\diagup\underset{CH_2-O}{\overset{CH_2-O}{\diagdown}}\overset{O}{\underset{H}{P}}$ | Iso-propanol | 3 hours/ 100° C. under autogenous pressure | 97.5% |
| 4 | $R_fCF=CHCH_2\overset{+}{\underset{C_2H_4OH}{\overset{CH_3}{N}}}-\overset{CH_3}{\underset{}{CH}}CH_2O\overset{O}{\underset{H}{P}}-O^-$ <br> $R_f$ as in Example 2 | $R_fCF=CHCH_2N\underset{C_2H_4OH}{\overset{CH_3}{\diagup}}$ <br> $O=P\underset{OCH_7}{\overset{OCH}{\diagup}}\overset{CH_3}{\underset{H}{\diagdown}}$ | Iso-propanol | 3 hours/ 100° C. under autogenous pressure | 97.3% |
| 5 | $C_7F_{15}CF=CHCH_2\overset{+}{\underset{CH_3}{\overset{H}{N}}}-CH_2-\underset{CH_3}{\overset{CH_3}{C}}-CH_2O-\overset{O}{\underset{H}{P}}-O^-$ | $C_7F_{15}CF=CHCH_2N\underset{CH_3}{\overset{H}{\diagup}}$ $\underset{CH_3}{\overset{CH_3}{C}}\diagup\underset{CH_2-O}{\overset{CH_2-O}{\diagdown}}\overset{O}{\underset{H}{P}}$ | without solvent | 5 hours/ 100° C. | 98.8% |
| 6 | $C_9F_{19}CF=CHCH_2-\overset{+}{\underset{CH_3}{\overset{CH_3}{N}}}-CH_2-\underset{CH_3}{\overset{CH_3}{C}}-CH_2O-\overset{O}{\underset{H}{P}}-O^-$ | $C_9F_{19}CF=CHCH_2-N\underset{CH_3}{\overset{CH_3}{\diagup}}$ $\underset{CH_3}{\overset{CH_3}{C}}\diagup\underset{CH_2-O}{\overset{CH_2-O}{\diagdown}}\overset{O}{\underset{H}{P}}$ | without solvent | 2 hours/ 140° C. | 98.8% |
| 7 | $C_5F_{11}CF=CHCH_2\overset{+}{\underset{C_2H_5}{\overset{C_2H_5}{N}}}-CH_2-\underset{C_6H_5}{\overset{CH_3}{C}}-CH_2O-\overset{O}{\underset{H}{P}}-O^-$ | $C_5F_{11}CF=CHCH_2-N\underset{C_2H_5}{\overset{C_2H_5}{\diagup}}$ $\underset{Ph}{\overset{CH_3}{C}}\diagup\underset{CH_2-O}{\overset{CH_2-O}{\diagdown}}\overset{O}{\underset{H}{P}}$ | without solvent | 3 hours/ 140° C. | 98.2% |
| 8 | $R_fCF=CHCH_2-\overset{+}{\underset{C_2H_4OH}{\overset{CH_3}{N}}}-CH_2CH_2O-\overset{O}{\underset{H}{P}}-O^-$ <br> $R_f$ as in Example 2 | $R_fCF=CHCH_2N\underset{C_2H_4OH}{\overset{CH_3}{\diagup}}$ $\underset{CH_2-O}{\overset{CH_2-O}{\diagup}}\overset{O}{\underset{H}{P}}$ | Iso-propanol | 2 hours/ 120° C. under autogenous pressure | 97.3% |
| 9 | $C_7F_{15}CF=CHCH_2\overset{+}{\underset{C_2H_5}{\overset{C_2H_5}{N}}}-\overset{CH_3}{\underset{}{CH}}-CH_2O-\overset{O}{\underset{H}{P}}-O^-$ | $C_7F_{15}CF=CHCH_2N\underset{C_2H_5}{\overset{C_2H_5}{\diagup}}$ <br> $CH_3-CH-O\diagdown\overset{H}{\underset{O}{P}}$ <br> $\quad\mid$ <br> $\quad CH_2-O\diagup$ | Iso-propanol | 4 hours/ 100° C. under autogenous pressure | 97.6% |

| Substance No. | Starting Formula | materials | Reaction Solvent | Reaction temperature time | Yield |
|---|---|---|---|---|---|
| 10 | $C_5F_{11}CF\!=\!CHCH_2\!-\!\overset{+}{\underset{C_2H_5}{\underset{|}{N}}}\!-\!\overset{C_2H_5}{\underset{|}{CH}}\!-\!CH_2O\!-\!\overset{O}{\underset{H}{\overset{\|}{P}}}\!-\!O^-$ (with CH$_3$ branch) | $C_5F_{11}CF\!=\!CHCH_2N(C_2H_5)_2$; $CH_3\!-\!CH\!-\!O\!\!\underset{CH_2\!-\!O}{\overset{}{\diagdown}}\!\!\overset{O}{\underset{H}{\overset{\|}{P}}}$ | Iso-propanol | 4 hours/ 100° C. under autogenous pressure | 97.0% |
| 11 | $R_f CF\!=\!CHCH_2\!-\!\overset{+}{\underset{C_2H_4OH}{\underset{|}{N}}}\!\!\overset{CH_3}{\underset{|}{}}\!-\!CH_2CH_2CH_2O\!-\!\overset{O}{\underset{H}{\overset{\|}{P}}}\!-\!O^-$<br>$R_f$ as in Example 2 | $R_f CF\!=\!CHCH_2N(CH_3)(C_2H_4OH)$; $CH_2\!-\!O\!\!\underset{CH_2\!-\!O}{\overset{CH_2}{\diagup}}\!\!\overset{O}{\underset{H}{\overset{\|}{P}}}$ | Iso-propanol | 2 hours/ 120° C. under autogenous pressure | 97.8% |
| 12 | $C_7F_{15}CF\!=\!CHCH_2\!-\!\overset{+}{\underset{C_2H_4OH}{\underset{|}{N}}}\!\!\overset{CH_3}{\underset{|}{}}\!-\!CH_2\!-\!\overset{CH_3}{\underset{CH_3}{\overset{|}{C}}}\!-\!CH_2O\!-\!\overset{O}{\underset{H}{\overset{\|}{P}}}\!-\!O^-$ | $C_7F_{15}CF\!=\!CHCH_2N(CH_3)(C_2H_4OH)$; $\overset{CH_3}{\underset{CH_3}{\overset{|}{C}}}\!\!\overset{CH_2\!-\!O}{\underset{CH_2\!-\!O}{\diagup\diagdown}}\!\!\overset{O}{\underset{H}{\overset{\|}{P}}}$ | without solvent | 4 hours/ 105° C. | 98.2% |
| 13 | $C_8F_{17}CH_2CH_2\!-\!\overset{+}{\underset{H}{\underset{|}{N}}}\!\!\overset{H}{\underset{|}{}}\!-\!CH_2CH_2O\!-\!\overset{O}{\underset{H}{\overset{\|}{P}}}\!-\!O^-$ | $C_8F_{17}CH_2CH_2NH_2$; $CH_2\!-\!O\!\!\underset{CH_2\!-\!O}{\diagup}\!\!\overset{O}{\underset{H}{\overset{\|}{P}}}$ | Iso-propanol | 5 hours/ 80° C. | 98.9% |
| 14 | $C_8F_{17}CH_2CH_2\!-\!\overset{+}{\underset{H}{\underset{|}{N}}}\!\!\overset{H}{\underset{|}{}}\!-\!CH_2CH_2CH_2O\!-\!\overset{O}{\underset{H}{\overset{\|}{P}}}\!-\!O^-$ | $C_8F_{17}CH_2CH_2NH_2$; $CH_2\!\!\underset{CH_2\!-\!O}{\overset{CH_2\!-\!O}{\diagup\diagdown}}\!\!\overset{O}{\underset{H}{\overset{\|}{P}}}$ | Iso-propanol | 5 hours/ 80° C. | 98.5% |
| 15 | $C_8F_{17}CH_2CH_2\!-\!\overset{+}{\underset{H}{\underset{|}{N}}}\!\!\overset{CH_3}{\underset{|}{}}\!-\!CH_2CH_2O\!-\!\overset{O}{\underset{H}{\overset{\|}{P}}}\!-\!O^-$ | $C_8F_{17}CH_2CH_2N(CH_3)(H)$; $CH_2\!-\!O\!\!\underset{CH_2\!-\!O}{\diagup}\!\!\overset{O}{\underset{H}{\overset{\|}{P}}}$ | Iso-propanol | 5 hours/ 80° C. | 97.2% |
| 16 | $C_6F_{13}CH_2CH_2\!\overset{+}{\underset{H}{\underset{|}{N}}}\!\!\overset{H}{\underset{|}{}}\!-\!CH_2\!\!\overset{CH_3}{\underset{CH_3}{\overset{|}{C}}}\!-\!CH_2O\!-\!\overset{O}{\underset{H}{\overset{\|}{P}}}\!-\!O^-$ | $C_6F_{13}CH_2CH_2NH_2$; $\overset{CH_3}{\underset{CH_3}{\overset{|}{C}}}\!\!\overset{CH_2\!-\!O}{\underset{CH_2\!-\!O}{\diagup\diagdown}}\!\!\overset{O}{\underset{H}{\overset{\|}{P}}}$ | Iso-propanol | 5 hours/ 80° C. | 98.6% |
| 17 | $(C_6F_{13}CH_2CH_2)_2\overset{+}{\underset{H}{\underset{|}{N}}}\!-\!CH_2CH_2O\!-\!\overset{O}{\underset{H}{\overset{\|}{P}}}\!-\!O^-$ | $(C_6F_{13}CH_2CH_2)_2NH$; $CH_2\!-\!O\!\!\underset{CH_2\!-\!O}{\diagup}\!\!\overset{O}{\underset{H}{\overset{\|}{P}}}$ | without solvent | 4 hours/ 120° C. | 92.0% (after recrystallization) Elementary analysis:<br>found: calculated:<br>C 26.3% 26.5%<br>H 1.7% 1.7%<br>N 1.8% 1.7%<br>F 60.4% 60.4%<br>P 3.7% 3.8% |

-continued

| Substance No. | Starting Formula | materials | Reaction Solvent | Reaction temperature time | Yield |
|---|---|---|---|---|---|
| 18 | (C₈F₁₇CH₂CH₂)₂N⁺H—CH₂—C(CH₃)₂—CH₂O—P(=O)(O⁻)(H) | (C₈F₁₇CH₂CH₂)₂NH; CH₃-C(CH₃)-(CH₂-O)₂P(=O)H (cyclic) | without solvent | 4 hours/ 120° C. | 94% (after recrystallization) found: calculated: C 28.9% 28.3% H 2.3% 1.9% N 1.4% 1.3% F 61.0% 58.7% P 3.2% 2.9% |
| 19 | R_fCF=CHCH₂—N⁺(CH₃)(C₂H₄OH)—CH₂—C(CH₃)(C₆H₅)—CH₂—O—P(=O)(O⁻)(H); R_f as in Example 2 | R_fCF=CHCH₂—N(CH₃)(C₂H₄OH); CH₃-C(C₆H₅)-(CH₂-O)₂P(=O)H (cyclic) | without solvent | 4 hours/ 140° C. | 97.4% |
| 20 | C₇F₁₅(CH₂)₃—N⁺(CH₃)(C₂H₄OH)—CH₂—C(CH₃)₂—CH₂—O—P(=O)(O⁻)(H) | C₇F₁₅(CH₂)₃—N(CH₃)(C₂H₄OH); CH₃-C(CH₃)-(CH₂-O)₂P(=O)H (cyclic) | without solvent | 5 hours/ 140° C. | 99% |
| 21 | R_fCF=CHCH₂—N⁺(C₂H₅)₂—CH₂—C(CH₃)₂—CH₂—O—P(=O)(O⁻)(H); R_f as in Example 2 | R_fCF=CHCH₂—N(C₂H₅)₂; CH₃-C(CH₃)-(CH₂-O)₂P(=O)H (cyclic) | without solvent | 3 hours/ 120° C. | 98.2% |

Nuclear magnetic resonance spectra for Examples 3 to 21:

EXAMPLE 3

$^1$H spectrum in CDCl$_3$

| | | | | |
|---|---|---|---|---|
| 12.05 1.62 | | H—P(=O) | doublet with a coupling constant of ~629 Hz | |
| 5.6 to 6.6: | | —CF=CH— | triplettized doublet | |
| 3.7 to 4.3: | | =CH—CH₂—N⁺< and HO₂P—OCH₂ | multiplets | |
| 2.7 to 3.3: | | —N⁺(CH₂—)(CH₂—)(CH₂—) | quartet and broad singlet | |
| 1.0 to 1.5: | | >N⁺(CH₂CH₃)₂ | triplet | |
| 0.9: | | >C(CH₃)₂ | singlet | |

$^{19}$F spectrum in CDCl$_3$

| | |
|---|---|
| 2.9: | —CF$_3$, |
| 38.5: | —CF$_2$—CF= |
| 42.0 to 44.5 | —(CF$_2$)$_4$— |
| 45.5: | —CF$_2$—CF= |
| 47.2: | CF$_3$—CF$_2$— |

$^{19}$F NMR spectrum in CDCl$_3$/1,1,2-trichloro-1,2,2-trifluoroethane (1:1)

| | |
|---|---|
| 30: | —CF$_3$ |
| 39.3: | —CF$_2$—CF= |
| 42.5 to 44.5: | —(CF$_2$)$_4$— |
| 45.0: | —CF$_2$—CF= |
| 47.8: | CF$_3$—CF$_2$— |

EXAMPLE 4

$^1$H spectrum in 1,1,2-trichloro-1,2,2-trifluoroethane.

| | | | |
|---|---|---|---|
| 11.9 1.5 | | \>P(=O)(H) | doublet, coupling constant of ~624 Hz |
| 6.8 | to | 7.1: —CH$_2$OH | broad singlet |
| 5.7 | to | 6.6: —CF=CH— | triplettized doublet |
| 3.8 | to | 4.4: =CH—CH$_2$—N$^+$\< | and HO$_2$P—OCH$_2$—multiplets |
| 2.9 | to | 3.2: \>N—CH$_2$—C\<, | \>N$^+$—CH— and —CH$_2$OH; singlet or multiplets |
| 2.6 | to | 2.7: \>N$^+$—CH$_3$ | |
| 1.1 | to | 1.4: \>CH—CH$_3$ | |

$^{19}$F spectrum in CHCl$_3$

| | |
|---|---|
| 3.5: | —CF$_3$ |
| 39.5: | =CF—CF$_2$— |
| 43.0 to 45.5: | —(CF$_2$)$_n$— |
| 46.0: | —CF$_2$—CF= |
| 48.2: | CF$_3$—CF$_2$— |

EXAMPLE 5

$^1$H spectrum in CDCl$_3$/1,1,2-trichloro-1,2,2-trifluoroethane (1:1)

| | | | |
|---|---|---|---|
| 12.2 1.5 | | \>P(=O)(H) | doublet, coupling constant 642 Hz |
| 8.0 | to | 8.7: —N$^+$H | broad, indistinct singlet |
| 5.6 | to | 6.7: —CF=CH— | triplettized doublet |
| 3.8 | to | 4.0: =CH—CH$_2$—N$^+$\< | multipet |
| 3.2 | to | 3.6: { HO$_2$P—OCH$_2$— , —N$^+$—CH$_2$—C(CH$_3$)$_2$— } | superimposing muliplets |
| 2.5 | to | 2:7 —N$^+$—CH$_3$ | singlet |
| 0.87: | | \>C(CH$_3$)$_2$ | singlet |

EXAMPLE 6

$^1$H NMR spectrum in CDCl$_3$/1,1,2-trichloro-1,2,2-trifluoroethane (1:1)

| | | |
|---|---|---|
| 12.17 1.55 | \>P(=O)(H) | doublet, coupling constant 637 Hz |
| 5.7 to 6.6: | —CF=CH— | triplettized doublet |

-continued

| | | | |
|---|---|---|---|
| 3.5 to 4.1: | =CH—CH$_2$—N$^+$⟨ | and —CH$_2$—OPO$_2$H | multiplets |
| 3.2 to 3.5: | ⟩N$^+$—CH$_2$C(CH$_3$)$_2$— | | multiplet |
| 2.75: | ⟩N$^+$(CH$_3$)$_2$ | | singlet |
| 0.86: | ⟩C(CH$_3$)$_2$ | | singlet |

$^{19}$F spectrum in CDCl$_3$/1,1,2-trichloro-1,2,2-trifluoroethane (1:1)

| | |
|---|---|
| 3.0: | CF$_3$— |
| 39.4: | —CF$_2$—CF= |
| 42.5 to 45.0: | —(CF$_2$)$_6$— |
| 45.5: | —CF$_2$—CF= |
| 48.0: | CF$_3$—CF$_2$— |

EXAMPLE 7

$^1$H NMR spectrum in 1,1,2-trichloro-1,2,2-trifluoroethane

| | | |
|---|---|---|
| 12.2, 1.6 | ⟩P(H)(=O) | doublet, coupling constant 636 Hz |
| 6.8 to 7.4: | C$_6$H$_5$— | multiplet |
| 5.4 to 6.4: | —CF=CH— | triplettized doublet |
| 3.5 to 4.4: | —CH$_2$—OP$_2$H, =CF—CH$_2$—N$^+$⟨ | multiplets |
| 2.8 to 3.2: | —N$^+$(CH$_2$—C⟨)(CH$_2$—CH$_3$)(CH$_2$—CH$_3$) | multiplets |
| 1.1 to 1.4: | ⟩C(CH$_3$)(C$_6$H$_5$) and ⟩N$^+$(CH$_2$CH$_3$)$_2$ | superimposed multiplets |

$^{19}$F spectrum in CHCl$_3$

| | |
|---|---|
| 2.9: | CF$_3$— |
| 39.0: | —CF$_2$—CF= |
| 43.5 to 45.0: | —(CF$_2$)$_2$—CF—CF= |
| 47.7: | CF$_3$—CF$_2$— |

EXAMPLE 8

$^1$H spectrum in 1,1,2-trichloro-1,2,2-trifluoroethane

| | | |
|---|---|---|
| 11.90, 1.63 | ⟩P(H)(=O) | doublet, coupling constant 616 Hz |
| 7.4 to 7.9: | —OH | broad singlet |
| 5.7 to 6.7: | —CF=CH— | triplettized doublet |
| 3.5 to 4.5: | —N$^+$(CH$_2$—)(CH$_2$—)(CH$_2$—) | —CH$_2$OH and HO$_2$POCH$_2$— superimposed multiplets |
| 2.7 to 2.8: | ⟩N$^+$—CH$_3$ | singlet |

$^{19}$F spectrum in CHCl$_3$

| | |
|---|---|
| 3.0: | —CF$_3$ |
| 39.0: | =CF—CF$_2$— |
| 43.0 to 44.2: | —(CF$_2$)$_n$— |
| 45.0: | =CF—CF$_2$— |
| 48.0: | CF$_3$—CF$_2$— |

EXAMPLE 9

$^1$H spectrum in 1,1,2-trichloro-1,2,2-trifluoroethane

| | | |
|---|---|---|
| 12.40, 1.51 | ⟩P(H)(=O) | doublet, coupling constant 653 Hz |
| 5.5 to 6.3: | —CF=CH— | triplettized doublet |
| 3.4 to 4.4: | CH$_2$—CH=, ⟩N$^+$(CH—CH$_3$) and —CH$_2$OP$_2$H | multiplets |
| 2.4 to 3.0: | ⟩N$^+$(CH$_2$CH$_3$)$_2$ | quartet |
| 1.0 to 1.5: | ⟩CH—CH$_3$ and ⟩N$^+$(CH$_2$CH$_3$)$_2$ | doublet, partially superimposed by a triplet |

$^{19}$F spectrum in CHCl$_3$

| | |
|---|---|
| 3.4: | —CF$_3$ |
| 39.2: | =CF—CF$_2$— |
| 43.0 to 45.0: | —(CF$_2$)$_4$— |
| 48.0: | CF$_3$—CF$_2$— |
| 49.0: | =CF—CF$_2$ |

EXAMPLE 10

$^1$H spectrum in 1,1,2-trichloro-1,2,2-trifluoroethane

| | | |
|---|---|---|
| 11.9, ~1.6 | ⟩P(H)(=O) | doublet, coupling constant 618 Hz |
| 5.8 to 6.8: | —CF=CH— | triplettized doublet |
| 3.5 to 4.2: | ⟩N$^+$(CH—CH$_3$)(CH$_2$—CH=) and —CH$_2$OP$_2$H | multiplets |
| 2.8 to 3.3: | ⟩N$^+$(CH$_2$CH$_3$)$_2$ | quartet |

| 1.0 to 1.6: | $\rangle$CH—CH$_3$ and $\rangle\overset{+}{\text{N}}$(CH$_2$CH$_3$)$_2$ | triplet superimposed by a doublet |

$^{19}$F spectrum in CHCl$_3$

| 2.6: | —CF$_3$ |
|---|---|
| 38.9: | =CF—CF$_2$— |
| 43.8 to 45.0: | =CF—CF$_2$—(CF$_2$)$_2$— |
| 47.5: | CF$_3$—CF$_2$— |

EXAMPLE 11

$^1$H spectrum in 1,1,2-trichloro-1,2,2-trifluoroethane

| 11.85 1.61 | $\rangle$P$\overset{\text{H}}{\underset{\text{O}}{\diagup}}$ | doublet, coupling constant 614 Hz |
| 7.8 to 8.3: | —OH | broad singlet |
| 5.70 to 6.70: | —CF=CH— | triplettized doublet |
| 3.5 to 4.4: | CH$_2$ —N$\overset{+}{\diagdown}$—CH$_2$—, CH$_2$— | —CH$_2$OH and CH$_2$OPO$_2$H superimposing multiplets |
| 2.7 to 2.8: | $\rangle\overset{+}{\text{N}}$—CH$_3$ | singlet |
| 1.3 to 1.5 | —CH$_2$—CH$_2$—CH$_2$— multiplet | |

$^{19}$F spectrum in CHCl$_3$

| 3.0: | —CF$_3$ |
|---|---|
| 39.0: | =CF—CF$_2$— |
| 42.5 to 45.5: | —(CF$_2$)$_n$—CF$_2$—CF= |
| 47.8: | CF$_3$—CF$_2$— |

EXAMPLE 12

$^1$H spectrum in CDCl$_3$/1,1,2-trichloro-1,2,2-trifluoroethane

| 12.15 1.55 | $\rangle$P$\overset{\text{H}}{\underset{\text{O}}{\diagup}}$ doublet with a coupling constant of 636 Hz |
| 7.8 to 8.2: | —CH$_2$OH broad singlet |
| 5.7 to 6.8: | —CF=CH— triplettized doublet |
| 3.8 to 4.4: | =CH—CH$_2$—$\overset{+}{\text{N}}$$\diagdown$ and HO$_2$P—OCH$_2$— multiplets |
| 2.8 to 3.4: | $\rangle\overset{+}{\text{N}}\diagdown$CH$_2$— CH$_2$— and —CH$_2$OH multiplets |
| 2.82: | $\rangle\overset{+}{\text{N}}$—CH$_3$ singlet |
| 0.82: | $\rangle$C(CH$_3$)$_2$ singlet |

$^{19}$F spectrum in CDCl$_3$/1,1,2-trichloro-1,2,2-trifluoroethane

| 3.3: | CF$_3$— |
|---|---|
| 38.3: | —CF$_2$—CF= |
| 42.5 to 45.0: | —(CF$_2$)$_4$—CF$_2$—CF= |
| 48.0: | CF$_3$—CF$_2$— |

EXAMPLE 13

$^1$H spectrum in CDCl$_3$

| 12.19 1.60 | $\rangle$P$\overset{\text{H}}{\underset{\text{O}}{\diagup}}$ doublet with a coupling constant of 635 Hz |
| 8.1 to 8.3: | $\rangle\overset{+}{\text{NH}}_2$ broad signal |
| 3.6 to 4.2: | —CH$_2$—O—PO$_2$H multiplet |
| 2.9 to 3.3: | $\rangle\overset{+}{\text{N}}\diagdown$CH$_2$— CH$_2$— multiplets |
| 2.0 to 3.3: | —CF$_2$—CH$_2$—CH$_2$— unresolved multiplet |

$^{19}$F spectrum in CHCl$_3$

| 3.1: | —CF$_3$ |
|---|---|
| 35.2: | —CF$_2$—CH$_2$— |
| 42.0 to 45.0: | —(CF$_2$)$_5$— |
| 47.7: | CF$_3$—CF$_2$— |

EXAMPLE 14

$^1$H spectrum in CDCl$_3$

| 12.14 1.60 | $\rangle$P$\overset{\text{H}}{\underset{\text{O}}{\diagup}}$ doublet with a coupling constant of 632 Hz |
| 8.3 to 9.2: | $\rangle\overset{+}{\text{NH}}_2$ broad signal |
| 3.8 to 4.2: | —CH$_2$—OPO$_2$H multiplet |
| 2.7 to 3.3: | $\rangle\overset{+}{\text{N}}\diagdown$CH$_2$— CH$_2$— superimposing multiplets |
| 2.0 to ~3.3: | —CF$_2$—CH$_2$—CH$_2$— unresolved multiplet |
| 1.2 to 1.5: | —CH$_2$—CH$_2$—CH$_2$— multiplet |

$^{19}$F spectrum in CHCl$_3$

| 3.4: | CF$_3$— |
|---|---|
| 35.3: | —CF$_2$—CH$_2$— |
| 42.0 to 45.5: | —(CF$_2$)$_5$— |
| 47.8: | CF$_3$—CF$_2$— |

EXAMPLE 15

¹H spectrum in CDCl₃

| | |
|---|---|
| 12.10<br>1.55 ⟩P(H)(=O) | doublet with a coupling constant of 633 Hz |
| 8.8 to 9.4: | ⟩⁺NH— broad signal |
| 3.8 to 4.2:<br>2.8 to 3.3: | —CH₂—OPO₂H multiplet<br>⟩⁺N(CH₂—)(CH₂—) unstructured multiplets |
| 2.6 to 2.7: | ⟩⁺NCH₃ singlet |
| 2.1 to 3.2: | —CF₂—CH₂— broad, unresolved multiplet |

¹⁹F spectrum in CDCl₃

| | |
|---|---|
| 2.6: | CF₃— |
| 34.6: | —CF₂—CH₂ |
| 42.0 to 45.0: | —(CF₂)₅— |
| 47.2: | CF₃—CF₂— |

EXAMPLE 16

| | |
|---|---|
| 12.10<br>1.40 ⟩P(H)(=O) | doublet |
| 6.5 to 7.0: | ⟩⁺NH₂ broad signal |
| 3.8 to 4.2:<br>2.9 to 3.4: | —CH₂—OPO₂H multiplet<br>⟩⁺N(CH₂—)(CH₂—) singlet and multiplet |
| 2.1 to 3.2: | —CF₂—CH₃— broad, unresolved multiplet |
| 0.9 to 1.1: | ⟩C(CH₃)₂ singlet |

¹⁹F spectrum in CDCl₃

| | |
|---|---|
| 2.6: | CF₃— |
| 35.0: | —CF₂—CH₂— |
| 42.5 to 45.0: | —(CF₂)₃— |
| 47.5: | CF₃—CF₂— |

EXAMPLE 19

¹H spectrum in CDCl₃

| | |
|---|---|
| 12.10<br>1.56 ⟩P(H)(=O) | doublet, coupling constant 638 Hz |
| 7.0 to 7.5: | C₆H₅ unstructured multiplet |
| 6.6 to 7.0: | OH— broad singlet |

-continued

| | |
|---|---|
| 5.4 to 6.5:<br>3.5 to 4.4: | —CF=CH— triplettized doublet<br>=CH—CH₂N⟨⁺ and |
| 2.8 to 3.4: | —CH₂—OPO₂H multiplets<br>⟩⁺N(CH₂—)(CH₂—) and —CH₂OH multiplets |
| 2.5: | ⟩⁺NCH₃ singlet |
| 1.1 to 1.3: | ⟩C(CH₃)₂ singlet |

¹⁹F spectrum

| | |
|---|---|
| 2.7: | CF₃— |
| 38.8: | —CF₂—CF= |
| 42.5 to 45.0: | —(CF₂)ₙ— |
| 45.5: | =CF—CF₂— |
| 47.7: | CF₃—CF₂— |

EXAMPLE 20

¹H spectrum in CDCl₃/1,1,2-trichloro-1,2,2-trifluoroethane

| | |
|---|---|
| 12.16<br>1.56 ⟩P(H)(=O) | doublet with coupling constant of 636 Hz |
| 3.8 to 4.2:<br>2.8 to 3.4: | —CH₂—OPO₂H unresolved multiplet<br>—⁺N(CH₂—)(CH₂—) and |
| 2.9: | —CH₂OH unresolved multiplets<br>⟩⁺NCH₃ singlet |
| 1.1 to 2.5: | —CF₂—CH₂—CH₂— broad, unresolved multiplet, partially superimposed by CH₂—CH₂—CH₂—N⁺⟨ |
| 0.8 to 0.9: | ⟩C(CH₃)₂ singlet |

¹⁹F spectrum in CDCl₃/1,1,2-trichloro-1,2,2-trifluoroethane

| | |
|---|---|
| 3.2: | CF₃— |
| 35.5: | —CF₂—CH₂— |
| 42.5 to 45.5: | —(CF₂)₄— |
| 48.0: | CF₃—CF₂— |

EXAMPLE 21

¹H spectrum in CDCl₃

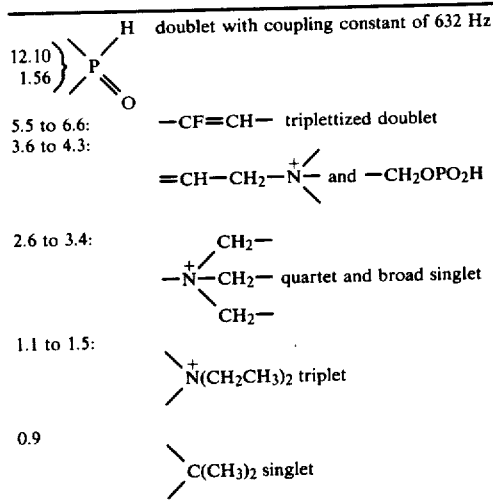

| Shift | Assignment |
|---|---|
| 12.10 / 1.56 | H doublet with coupling constant of 632 Hz, $\diagdown P \diagup$ / $\diagdown O$ |
| 5.5 to 6.6 | —CF=CH— triplettized doublet |
| 3.6 to 4.3 | =CH—CH$_2$—$\overset{+}{N}$— and —CH$_2$OPO$_2$H |
| 2.6 to 3.4 | —$\overset{+}{N}$(CH$_2$—)$_3$ quartet and broad singlet |
| 1.1 to 1.5 | $\diagdown \overset{+}{N}$(CH$_2$CH$_3$)$_2$ triplet |
| 0.9 | $\diagdown$C(CH$_3$)$_2$ singlet |

$^{19}$F spectrum in CHCl$_3$

| Shift | Assignment |
|---|---|
| 3.0 | CF$_3$— |
| 38.4 | —CF$_2$—CF= |
| 42.0 to 45.5 | —(CF$_2$)$_n$—CF$_2$—CF= |
| 47.3 | CF$_3$—CF$_2$— |

Amongst the fluorinated surface-active agents hitherto known, the ampholytic, fluorine-containing esters of phosphorous acid of the formula I, according to the invention, are distinguished by a high surface-active effectiveness. This is shown by the measured surface tension values determined in water (see Table No. 1). Here and in the following text, the compounds are compared with the following 6 fluorine-containing surface-active agents of the state of the art, which contain ester groups of acids of phosphorus and/or quaternary nitrogen:

V1: Ammonium bis-(N-ethyl-2-perfluoro-octyl-sulfonamidoethyl) phosphate with at most 15% of ammonium mono-(N-ethyl-2-perfluorooctyl-sulfonamidoethyl) phosphate (compare U.S. Pat. No. 2,803,656).

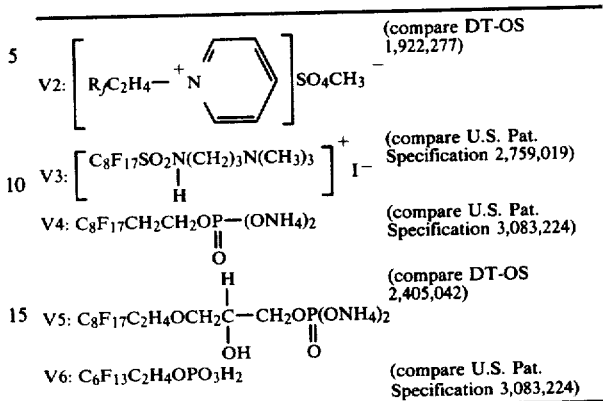

V2: $\left[ R_fC_2H_4-\overset{+}{N}\bigcirc \right] SO_4CH_3^-$ (compare DT-OS 1,922,277)

V3: $\left[ C_8F_{17}SO_2N(CH_2)_3N(CH_3)_3 \atop H \right]^+ I^-$ (compare U.S. Pat. Specification 2,759,019)

V4: $C_8F_{17}CH_2CH_2OP\underset{O}{\overset{\|}{-}}(ONH_4)_2$ (compare U.S. Pat. Specification 3,083,224)

V5: $C_8F_{17}C_2H_4OCH_2\underset{OH}{\overset{H}{C}}-CH_2OP\underset{O}{\overset{\|}{(ONH_4)_2}}$ (compare DT-OS 2,405,042)

V6: $C_6F_{13}C_2H_4OPO_3H_2$ (compare U.S. Pat. Specification 3,083,224)

Table No. 1

Measured surface tension values at 20° C. in mN/m, measured by the 'du Nouy tensiometer method' (draft DIN 53,914) in aqueous solution

| Example | Concentration (g/l) 5 | 1 | 0.3 | 0.1 | 0.03 | 0.01 | F content in the active substance | The product was present as |
|---|---|---|---|---|---|---|---|---|
| 1 | 20 | 22 | 27 | 37 | 47 | 60 | 41.5% | Oil with 100% of active substance |
| 2 | 19 | 19 | 20 | 23 | 29 | 45 | 44.0% | Oil with 100% of active substance |
| 2a | 19 | 20 | 22 | 23 | 30 | 43 | 44.0% | 2 as a solution in isopropanol with 50% by weight of active substance |
| 3 | 20 | 20 | 23 | 35 | 46 | 53 | 46.8% | Oil with 100% of active substance |
| 4 | 18 | 19 | 20 | 23 | 28 | 34 | 47.5% | Oil with 100% of active substance |
| 5 | 17 | 18 | 22 | 33 | 48 | 59 | 50.1% | Oil with 100% of active substance |
| 6 | 19 | 20 | 25 | 35 | 55 | 56 | 52.7% | Oil with 100% of active substance |
| 7 | 21 | 24 | 28 | 32 | 37 | 46 | 37.3% | Oil with 100% of active substance |
| 8 | 18 | 18 | 20 | 22 | 33 | 47 | 48.7% | Oil with 100% of active substance |
| 11 | 16 | 17 | 19 | 21 | 29 | 37 | 47.5% | Oil with 100% of active substance |
| 19 | 18 | 19 | 21 | 23 | 30 | 44 | 41.3% | Oil with 100% of active substance |
| 20 | — | 20 | 22 | 24 | 29 | 43 | 44.8% | Oil with 100% of active substance |
| V1 | 22 | — | 47 | 48 | 62 | 63 | 21%, relative to the solution | 36% strength by weight solution in isopropanol/water |
| V2 | 22 | 23 | 35 | 46 | 56 | 57 | 49.8% | 100% of active substance |
| V3 | 18 | 18 | 19 | 21 | 25 | 33 | 41.1% | 100% of active substance |
| V4 | 27 | 31 | 43 | 54 | 66 | — | 22.4%, relative to the solution | 34.5% by weight in 1:1 isopropanol/water |
| V5 | 20 | 21 | 24 | 35 | 42 | 46 | 11.6%, relative to the solution | 19.9% by weight in isopropanol/water |

A further interesting property of the compounds according to the invention is their foaming behaviour (Table No. 2). The foam formation test according to Ross-Miles shows that, in the compounds according to the invention, the foaming power can be controlled by the chain length of the perfluoroalkyl radical. In addition to the weak foamers No. 1 and No. 7 having C$_5$F$_{11}$ radicals, there are the strongly foaming products No. 3 and No. 4 having C$_7$F$_{15}$ radicals. The product No. 2 or 2a with mixtures of perfluoroalkyl chains of C$_5$-C$_{11}$ shows a medium foaming behaviour. The foaming power can be increased by omitting branches at the methyl groups adjacent to the phosphite group (comparison between compounds No. 8 and No. 2). As a result of their different foaming behaviour, the fluorinated surface-active agents according to the invention are available as tailor-made products for various applications. Thus, strongly foaming surface-active agents are employed for cleaning agents, whilst weak foamers having good values for lowering the surface tension are employed in aqueous phase for degreasing metal parts in electroplating lines.

| Example | Foam height (mm) at | | | |
|---|---|---|---|---|
| | 25° C. | | 70° C. | |
| | 0 minutes | 5 minutes | 0 minutes | 5 minutes |
| 1 | 10 | 0 | 10 | 0 |
| 2 | 75 | 70 | 30 | 25 |
| 2a | 65 | 65 | 85 | 85 |
| 3 | 150 | 140 | 80 | 30 |
| 4 | 50 | 50 | 35 | 35 |
| 5 | 190 | 190 | 240 | 240 |
| 6 | 90 | 90 | 160 | 160 |
| 7 | 10 | 0 | 10 | 0 |
| 8 | 150 | 140 | 160 | 160 |
| 11 | 180 | 180 | 220 | 220 |
| V1 | 0 | 0 | 5 | 0 |
| V2 | 240 | 240 | 200 | 190 |
| V3 | 100 | 100 | 260 | 260 |

Due to their surface properties, the ampholytic fluorinated phosphites according to the invention are widely used as surface-active agents in the textile industry for wetting and cleaning. Table No. 3 describes the wetting power of the products according to the invention towards cotton and wool in an aqueous system. The determination was carried out in accordance with an immersion wetting test in the following manner:

Determination of the immersion wetting power:

A disc (about 35 mm $\phi$) of the test fabric is introduced into the test solution (600 ml beaker, tall type) by means of an immersion clamp in such a way that it is held about 30 mm above the bottom and 40 mm below the surface of the liquid. The disc sinks to the bottom when the air has been displaced from the fabric. The time from the immersion to the start of sinking is measured by means of light beams which are connected to a switch box (Viscomatik instrument). The pair of light beams is arranged in such a way that the determination of time corresponds to the DIN 53,901 method.

| Example | Sinking time (seconds) | | | |
|---|---|---|---|---|
| | Cotton | | | Wool |
| | 25° C. | 50° C. | 70° C. | 25° C. |
| 1 | 175 | 165 | 75 | 13 |
| 2 | 145 | 100 | 60 | 18 |
| 3 | 180 | 130 | 80 | 17 |
| 4 | >300 | 235 | 95 | 8 |
| 5 | 105 | 90 | 65 | 18 |
| 6 | >300 | 155 | 75 | 6 |
| 7 | >300 | >300 | 180 | 25 |
| 8 | 135 | 165 | 95 | 14 |
| 9 | 115 | 75 | 50 | 17 |
| 11 | 45 | 30 | 25 | 7 |
| 19 | 50 | 40 | 12 | 6 |
| V1 | >300 | >300 | >300 | >300 |
| V2 | 270 | 135 | 65 | 7 |
| V3 | 300 | 165 | 45 | 13 |

Due to their good wetting power, the compounds according to the invention can be used as dry-cleaning detergents. Dry-cleaning detergents are interface-active substances which enhance the cleaning action of organic solvents and broaden this action since hydrophilic soilings are also dealt with as the result of incorporating water into the organic medium. Table No. 4 shows the results of cleaning experiments in perchloroethylene. The cleaning experiments were carried out in the following manner:

Description of the procedure in the cleaning experiments:

Four series of artificially soiled standard test fabrics, in each case cotton, wool, polyester fabric and polyacrylonitrile fabric, manufactured by Testfabrics Inc. Middlesex, Ill. (USA) (soiling: iron oxide, carbon black, starch and oil) are successively cleaned in the same cleaning liquor in the laboratory. Cleaning is carried out in 400 ml of perchloroethylene liquors on fabrics which were conditioned beforehand under the action of atmospheric humidity in order to produce comparable conditions, corresponding to the so-called Lini test (in analogy to DIN Standard 54,024). The concentration of the fluorinated surface-active agents is 0.5 g/l and the temperature is 30° C.

The cleaning action is determined as % brightening in accordance with the formula $$A = 100 \cdot (W_g - W_a)/(W_o - W_a)$$

$W_o$ = reflectance of the unsoiled original fabric
$W_g$ = reflectance of the soiled fabric
$W_a$ = reflectance of the soiled fabric after cleaning The graying of the unsoiled original fabric, also treated, is determined in accordance with the formula $$V = 100 \cdot (W_o - W_v)/W_o$$

$W_o$ = reflectance of the unsoiled original fabric
$W_v$ = reflectance of the cleaned sample On the basis of the brightening and graying values obtained, the products according to the invention are superior to the comparative products V2 and V6.

The compounds of the formula I, according to the invention, are also suitable for use as additives to fire-fighting agents based on synthetic foam, in particular in combination with other fluorine-containing surface-active agents.

Table 4

Results of the cleaning experiments in perchloroethylene with various fluorinated surface-active agents (test fabrics conditioned, before cleaning, for 24 hours at 80% relative atmospheric humidity and 20° C.). B = Brightening, G = Graying

| | Perchloroethylene without additive | | Product from Example 1 | | Product from Example 2 | | Product V2 | | Product V6 | |
|---|---|---|---|---|---|---|---|---|---|---|
| | % B | % G | % B | % G | % B | % G | % B | % G | % B | % G |
| Series I. | | | | | | | | | | |
| Cotton | 2 | 1.9 | 3 | 2.3 | 4.7 | 1.2 | 6.5 | 7 | 0.4 | 10.9 |
| Wool | 5.8 | 0.0 | 10.8 | 0.8 | 15.8 | 0.4 | 0 | 18 | 10.5 | 5.3 |
| Polyester fabric | 5.5 | 0.7 | 4.4 | 1.9 | 6.4 | 1.1 | | | 5 | 2.0 |
| Polyacrylonitrile fabric | 5.0 | 3.3 | 6.5 | 5.2 | 8.1 | 3.4 | | | 4.2 | 7.7 |

Table 4-continued

Results of the cleaning experiments in perchloroethylene with various fluorinated surface-active agents (test fabrics conditioned, before cleaning, for 24 hours at 80% relative atmospheric humidity and 20° C.). B = Brightening, G = Graying

| | Perchloro-ethylene without additive | | Product from Example 1 | | Product from Example 2 | | Product V2 | | Product V6 | |
|---|---|---|---|---|---|---|---|---|---|---|
| | % B | % G | % B | % G | % B | % G | % B | % G | % B | % G |
| Series II. | | | | | | | | | | |
| Cotton | 3 | 4.7 | 2.6 | 3.7 | 4.5 | 1.3 | 1.0 | 16 | 0.4 | 11 |
| Wool | 5 | 2 | 10 | 3 | 15.2 | 0.6 | 3.0 | 12 | 10 | 10.8 |
| Polyester fabric | 6 | 1.5 | 3 | 2.6 | 5.9 | 1.7 | | | 4.8 | 3.8 |
| Polyacrylonitrile fabric | 6.1 | 2.9 | 5.5 | 3.2 | 7.7 | 3.5 | | | 4.1 | 8.3 |
| Series III. | | | | | | | | | | |
| Cotton | 3.1 | 5.5 | 2.7 | 5.4 | 4.8 | 1.7 | 2.5 | 12 | 1.8 | 13.8 |
| Wool | 5.8 | 0 | 11.7 | 3.3 | 15.6 | 0.7 | 10.0 | 12.2 | 11.1 | 12.2 |
| Polyester fabric | 5 | 4.1 | 3.5 | 5.1 | 5.7 | 2.0 | | | 3.4 | 3.7 |
| Polyacrylonitrile fabric | 5.3 | 4.8 | 5 | 6.1 | 7.5 | 3.9 | | | 5 | 9.7 |
| Series IV. | | | | | | | | | | |
| Cotton | 3 | 7.1 | 2.6 | 8 | 4.2 | 2.3 | 1 | 13 | 0.8 | 13.4 |
| Wool | 5.9 | 1.1 | 10.6 | 2.7 | 15.1 | 1.0 | 9.0 | 1.5 | 13.1 | 11.8 |
| Polyester fabric | 5.6 | 4.8 | 3.5 | 6.7 | 5.5 | 2.8 | | | 4.5 | 8.8 |
| Polyacrylonitrile fabric | 5.0 | 5.7 | 5 | 5.4 | 7.8 | 3.6 | | | 4.5 | 10.1 |

What is claimed:

1. Ampholytic, fluorine-containing esters of phosphorous acid of the general formula

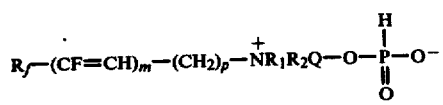
(I)

in which $R_f$ represents a perfluoroalkyl radical having 3 to 16 C atoms, $R_1$ and $R_2$ which can be identical or different represent hydrogen atoms, short-chain alkyl radicals having 1 to 4 C atoms, cyclohexyl radicals, 2-hydroxyalkyl radicals or the radical $R_f-(CF=CH)_m-(CH_2)_p-$ and Q represents alkylene radicals $-(CH_2)_x-$ with x = 2 or 3 and alkylene radicals $-CH_2CHR-$ or $-CH_2CRR'-CH_2$ with R and R' being a short-chain alkyl radical or a phenyl radical, it also being possible for R' to be H, and in which, furthermore, m is 0 or 1 and p is an integer from 1 to 4.

* * * * *